United States Patent [19]

Pagano et al.

[11] Patent Number: 4,487,071

[45] Date of Patent: Dec. 11, 1984

[54] FLAW DETECTION SYSTEM FOR RAILROAD RAILS AND THE LIKE

[75] Inventors: Dominick A. Pagano, Weston; Kevin S. Morris, New Milford, both of Conn.

[73] Assignee: Dapco Industries, Inc., Ridgefield, Conn.

[21] Appl. No.: 421,472

[22] Filed: Sep. 22, 1982

[51] Int. Cl.³ ............................................. G01N 29/04
[52] U.S. Cl. ........................................ 73/612; 73/631; 73/636
[58] Field of Search ................ 73/609, 610, 611, 612, 73/615, 625, 631, 636

[56] References Cited

U.S. PATENT DOCUMENTS

| | | | |
|---|---|---|---|
| 4,031,743 | 6/1977 | Kossoff et al. | 73/631 |
| 4,050,292 | 9/1977 | Bloch | 73/636 X |
| 4,137,776 | 2/1979 | Rudis et al. | 73/615 |
| 4,205,553 | 6/1980 | Rudis et al. | 73/615 |

*Primary Examiner*—James J. Gill
*Attorney, Agent, or Firm*—Lieberman Rudolph & Nowak

[57] ABSTRACT

Rail testing apparatus, particularly useful at the point of manufacture, for detecting flaws in railroad rails. A number of transducers transmit ultrasonic sound waves into a rail under test and receive the associated echo signals. The apparatus advantageously divides the rail into a plurality of measured rail segments and the amount of amplification applied to the associated echo signals may be varied over each rail segment, thus providing the ability to selectively increase or decrease the sensitivity of the testing apparatus. The amplified echo signals are selectively applied to detection apparatus with a positive and negative gating scheme to increase system accuracy and reliability.

8 Claims, 10 Drawing Figures

FLAW DETECTION SYSTEM FOR RAILROAD RAILS AND THE LIKE

FIELD OF THE INVENTION

This invention relates to detection apparatus and more particularly to ultrasonic flaw detection apparatus for use in detecting flaws in railroad rails or the like.

BACKGROUND OF THE INVENTION

Various systems are presently known which are directed to the rapid or automatic detection of flaws in railroad rails or the like. Such systems are generally directed to the use of automatic or semi-automatic equipment that will detect flaws as a testing vehicle travels along the rail. Due to increasing labor costs, along with increased maintenance requirements, automatic rail detection systems have essentially become mandatory since the cost of manual detection is becoming prohibitive.

One known apparatus used to detect flaws in railroad rails operates on the principal of introducing high frequency (ultrasonic) sound waves into the top or side of the rail and measuring the time period required for the sound wave to rebound from the bottom or opposite side of the rail. Any discontinuity within the rail, or the air/rail interface at the side or bottom of the rail itself, will reflect the sound wave and thus the time it takes for the reflected sound wave to return to a receiver is an indication of a discontinuity (flaw) within the rail or an expected return from the bottom or side of the rail. For example, with a flawed rail, the time required for the high frequency or ultrasonic pulse to rebound is less than would be expected in a normal rail as the occurrence of the flaw causes the ultrasonic sound wave to return earlier than expected since the wave did not travel through the full height or width of the rail.

One ultrasonic rail flaw detection system is described in U.S. Pat. No. 4,004,455 granted to Chester W. McKee et al on Jan. 25, 1977. This system (described in greater detail below) utilizes an ultrasonic transducer mounted in a fluid filled wheel of conventional design and the transducer transmits high frequency sound waves into the rail as the testing car and associated fluid filled wheel travel along the track. The sound waves are reflected within the rail and the return signals are detected and forwarded to counting and other circuitry to detect the presence of flaws emanating from defective areas of the rail. This system, although providing a useful and unique method for automatically detecting flaws in railroad rails is particularly adapted for detecting flaws, in the bolt hole areas of railroad rails during an on-site inspection but lacks the ability to enhance system sensitivity for particular rail areas or segments requiring higher inspection standards.

That is, it is known that railroad companies are instituting tighter specifications for new rails that will allow them to weld rails on site without risking the danger of incurring defects, particularly in the first 18 inches of a rail which forms a heat-affected zone adjacent to the welds. Therefore, from a rail manufacturers standpoint, it has become extremely important that the first and last 18 inches of any rail be inspected with much tighter specifications than the rest of the rail. This is necessary because if any defect, regardless how small, is located within the first 18 inches of the rail when the welding process takes place, those defects, such as slag inclusions, pipe, segregation etc., will literally blow up or expand resulting in premature failure of the rail and/or the weld.

It is, therefore, an object of the instant invention to provide rail inspection equipment with the ability to focus on particular rail segments and increase, at will, system sensitivity in these segments.

It is another object of the instant invention to provide rail inspection capability at the point of rail manufacture to detect potential flaws prior to a rail being delivered to the railroad for installation.

It is a further object of the instant invention to permit increased rail inspection capability for various rail segments with the sensitivity of the testing procedure being variable for each seperate rail segment.

It is a still further object of the instant invention to permit a rail manufacturer to inspect with increased sensitivity, particular rail segments, with the particular segment being inspected, and system sensitivity for that segment, being subject to operator control.

Yet another object of the instant invention is to provide such improved rail inspection apparatus which is readily fabricated at low cost from commercially available components.

SUMMARY OF THE INVENTION

In accordance with the invention, railroad rail inspection apparatus is provided in which an ultrasonic transducer transmits signals into a rail under test and receives associated echo signals from within the rail to detect the presence of rail flaws.

It is a feature of the invention that the inspection apparatus divides the rail under test into a plurality of measured rail segments.

It is another feature of the invention that the associated echo signals are supplied with varying amounts of amplification, with the amount of amplification being variable for each rail segment, such that the sensitivity of the inspection apparatus can vary over the length of the rail under test.

It is still another feature of the invention that the amplified echo signals are selectively gated to flaw detection apparatus wherein positive gating circuits supply unexpected echo signals (e.g. flaw indications) to the flaw detection apparatus while negative gating circuits supply expected echo signals (e.g. boundary information) to the flaw detection apparatus.

It is a still further feature of the invention that the presence of unexpected echo signals is indicative of rail flaws within the rail under test, while the absence of expected echo signals is indicative of loss of signal from the rail under test.

The foregoing and other objects and features will be more fully understood from the following description of an illustrative embodiment thereof in conjunction with the accompanying drawings.

DETAILED DESCRIPTION

The instant invention is concerned with a rail testing system at the point of manufacture which can be programmed by the operator to view each rail under test as a series of rail pieces, or segments, in which the system gain or sensitivity can be set to one of two preprogrammed values, high or low, for each rail segment. The system includes a micro-processor to continually monitor a rail sensor unit which indicates the presence, or absence, of a rail in the test unit and when a rail enters the test unit a shaft encoder rides on the rail and sends distance pulses to the micro-processor which in turn uses this information to define the rail segments. Both system gain for each segment under test and the number of segments per rail can be programmed by the system operator.

Through use of the invention a rail manufacturer can guarantee the integrity of the product of the customer while maintaining tight controls on the manufacturing process. Also the manufacturer can customize the rail testing procedure for each customer in accordance with customer requirements and rail quality.

Figure 1:
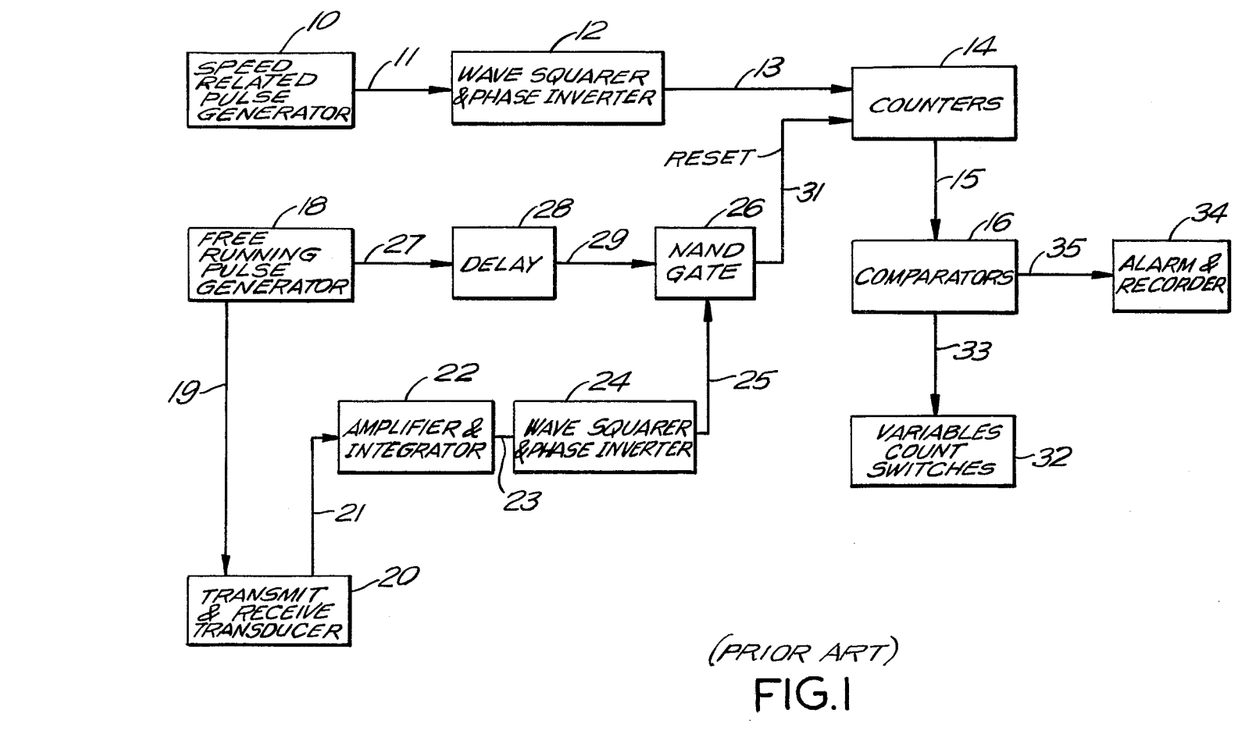
FIG. 1 illustrates a schematic block diagram of a prior art rail inspection system.

Before proceeding to a detailed description of the instant invention, it is helpful to describe the on-site rail testing system described in U.S. Pat. No. 4,004,455. The system described in this patent is designed to detect on site rail flaws through use of a vehicle which travels down the rail and transmits ultrasonic pulses into the rail for detection. The ultrasonic pulses are applied to the rail by transducers contained in a fluid filled wheel riding on the rail and the return signals from the transducer are utilized by the equipment to indicate the presence of flaws. Turning first to FIG. 1, there is shown a schematic block diagram of the apparatus described in U.S. Pat. No. 4,004,455, the teachings of which are expressly incorporated herein by reference. The apparatus of FIG. 1 includes a pulse generator 10 that has an output related to the speed of the fluid filled wheel moving over the track. Pulse generator 10 has its output connected by line 11 to a wave squarer and phase converter 12, with the wave squarer being a schmidt trigger or the like. The output of wave squarer and phase inverter 12 is connected by line 13 to drive one or more counters 14, which are in turn connected by line 15 to a comparative circuit 16.

A second pulse generator 18, which is free running and therefore independent of pulse generator 10, is connected through line 19 to drive a transmit and receive transducer 20. The transducer transmits ultrasonic pulses, which are applied to the rail through a fluid filled wheel (not shown), and the return signals are received by the same transducer. Return signals are fed through line 21 to amplifier and integrator 22 and then through line 23 to a wave squarer (which also may be a schmidt trigger or the like) and phase inverter 24, where the signal is shaped and inverted before being applied through line 25 to one input of a nand gate 26. The second input of the nand gate comes from pulse generator 18 through line 27, delay circuit 28 and line 29.

A pulse generated by pulse generator 18, is applied to both transducer 20 and delay circuit 28, which is preferably adjustable to accommodate differing rail dimensions. If a return signal received by transducer 20 is a reflected signal from the bottom of the rail, i.e. the signal has traveled the full height of the rail rather than from an intermediate point, approximately 60 microseconds will have elapsed from the time of transmission for a standard 133 pound rail. Therefore, if delay circuit 28 is preset for a 60 microsecond delay, then both inputs of the nand gate 26 will be simultaneously satisfied and will produce a reset pulse to the counter 14. Similarly if a flaw within the rail causes a pulse to be reflected from an intermediate point in the rail the reflected pulse will be received in a time period that is less than 60 microseconds. When this occurs the two inputs to nand gate 26 will not be simultaneously satisfied and an output reset pulse will not be produced.

It should be understood that the pulses that are transmitted and received by the transducer are not related to the speed or distance traversed by the fluid filled wheel and, therefore, do not provide an indication of the size of the flaw. The received signal indicates whether the signal has been reflected from either the bottom of the rail, in which case a reset signal is produced, or from an intermediate point, in which case the reset signal is not produced. To provide an indication of flaw size comparators 16 have one input provided by counters 14, which are driven by the speed related pulse generator 10, and another input provided by a variable count presetable switches 32 through line 33. Since switches 32 have adjustable settings to vary the preset counts, a count slightly larger, for example, than the known size of a bolt hole may be preset so that alarm and recorder 34 will not be actuated through line 35 unless the count accumulated in counter 14 exceeds the count that is preset on the variable count switches, indicating that the bolt hole is oversized and a flaw is present. Speed related pulse generator 10 provides a pulse for each incremental distance traversed by the fluid filled wheel and preferably provides a pulse every 1/16th of an inch.

More particularly, when a flaw in the rail is encountered by the apparatus, a reset pulse from nand gate 26 will not be generated and speed related pulse generator 10 will continually upcount counters 14. The output of counters 14 are applied to comparator 16 and the comparators 16 compare the count from counters 14 against the count from the preset variable switches 32, so that when the counts are equal an output is generated to alarm and recorder 34. Since it is desirable, in some applications, not to provide an alarm and record a flaw for the bolt holes themselves, the variable counts may be preset to be slightly larger than the bolt hole diameters so that an alarm is not sounded before the count of the counters 14 reaches and exceeds the count from the switches 32. By setting switches 32 to reflect a slightly oversized diameter, a normal bolt hole will not cause an alarm and only a crack emanating from a bolt hole will be effective in providing an alarm indication as is desired.

The instant invention operates on similar principals as those described above with respect to FIG. 1, but includes a number of improvements and refinements making the instant invention particularly suitable for testing rails at a manufacturing site.

Figure 2A:
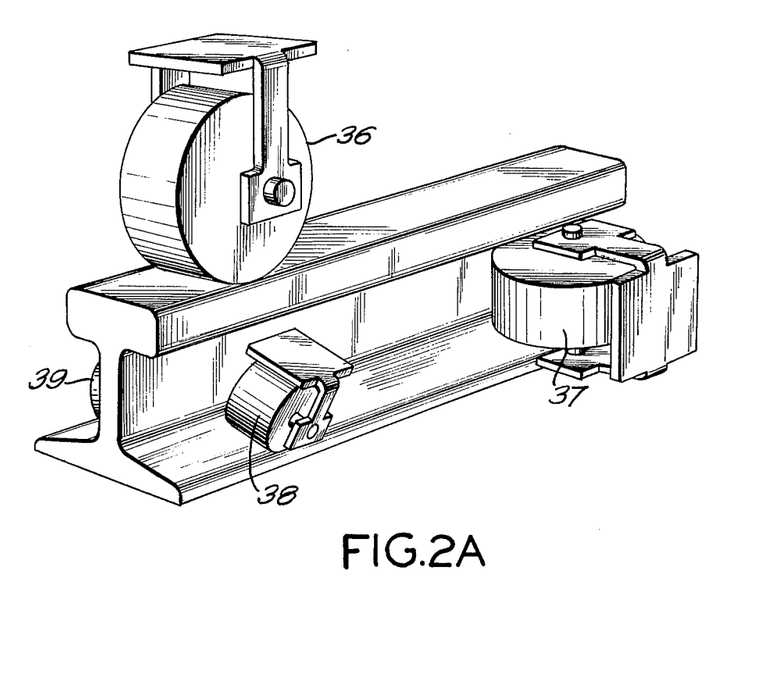
FIG. 2A illustrates the arrangement of transducers used with the rail inspection system of the instant invention.
Figure 2B:
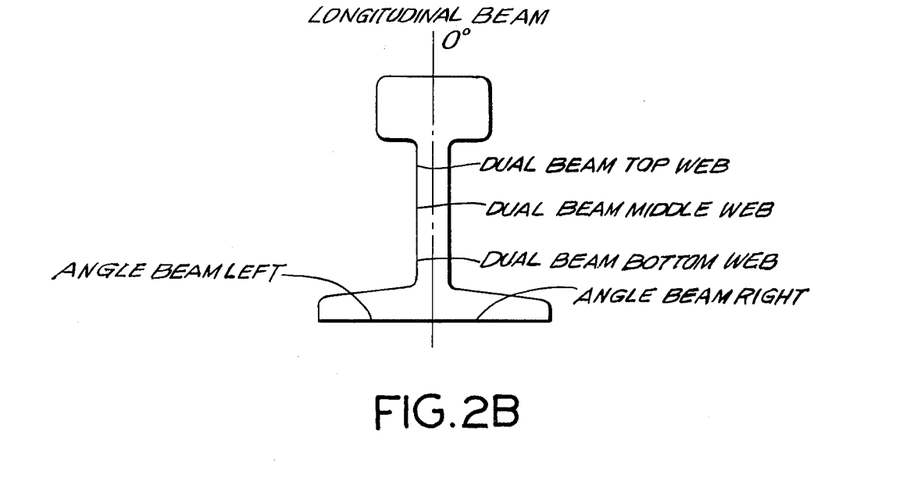
FIG. 2B is an end view of a rail under test illustrating the transducer arrangement.

Referring now to FIGS. 2A and 2B, the system of the instant invention utilizes six ultrasonic transducers for inspection of the head, web and base areas of a rail. More particularly in FIG. 2A there is illustrated the orientation of the fluid filled wheels (which include the transducers) utilized to achieve rail inspection. Wheel transducer 36 applies an ultrasonic pulse at the rail head to provide a longitudinal beam, wheel transducer 37 contains three separate dual transducers for testing the web area of the rail and wheel transducers 38 and 39 contain a single transducer for inspecting the bottom of the rail. FIG. 2B illustrates the various beam directions for each of the six transducers. In a preferred embodiment of the invention, transducer wheels 36 and 38 contain single transducers well known in the art, while transducer wheel 37 contains three dual beam transducers of the type for example described in U.S. Pat. No. 3,325,781 granted to R. V. Harris on June 13, 1967.

In operation transducer wheels 36, 37, 38 and 39 are moved over the rail under test and the ultrasonic transducers contained therein are simultaneously fired to transmit ultrasonic pulses into the rail under test. Not shown in FIG. 2A is a shaft encoder, which transmits pulses to the circuitry discussed below every 1/16th of an inch of wheel transducer travel over the rail. The manner in which a rail is moved from a manufacturing site to a test site can be accomplished in a number of ways all of which would be familiar to one skilled in the art and thus are not discussed herein. Similarly, the manner in which the rail would be loaded into the test unit and synchronization of the test equipment with the beginning of a rail are all well known and not described in detail.

Figure 3:
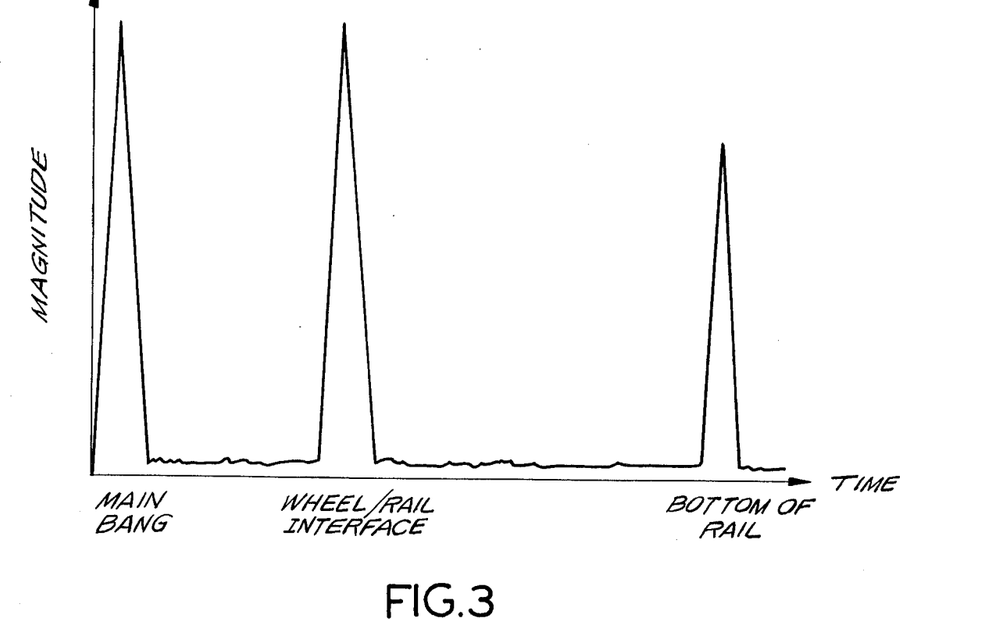
FIG. 3 is a time vs. magnitude plot for a response from one transducer used with the instant invention.

FIG. 3 illustrates a typical time versus response magnitude plot for a longitudinal beam transducer "fired" through a non-anomalous (i.e. non-flawed) section of rail. The time between the transducer firing (main bang) and the transducer wheel/rail interface is twice the length of time the ultrasound takes to travel from the transducer through the fluid filled wheel to the rail. After the transducer wheel/rail interface, the ultrasound wave is traveling inside the rail heading for the rail bottom. Once encountering the rail base the steel-/air interface causes a large ultrasonic reflection backup through the rail towards the transducer. When the energy from this reflection is detected by the transducer, it causes the bottom of a rail response as shown in FIG. 3.

The time from the main bang to the bottom of the rail response is twice the ultrasound wave travel time to the bottom of the rail. By knowing the distance from the top of the rail head to the bottom of the rail, the approximate time from the interface to the bottom of the rail and back is computed by;

$$t = \frac{2 \times L}{S} \text{ (in } \mu S\text{)}$$

where:
t is the time in microseconds,
L is the length from top of rail to bottom of rail in millimeters, and
S is the speed of a longitudinal wave in steel (6 millimeters per microsecond).

This equation is not only valid for the longitudinal transducer, but is valid for the system dual beam web transducers as well. The base angle beam transducers have no expected response, due to the nature of their orientation, as shown in FIGS. 2B. For unexpected responses (detected flaws) in this area, however, the above equation can be solved for L to determine the length of the depth of the response. The speed of the ultrasound waves is also different for these transducers:

$$L = \frac{tr}{2} \times S$$

where:
tr equals time of response measured from interface in microseconds,
S equals shear wave speed of ultrasound in steel (3.2 millimeters per microsecond), and
L equals depth of response in millimeters.

The six ultrasonic transducers referred to above permit the system to detect a total of ten alarm conditions. The ten alarm conditions are described in Table 1 below.

| Transducer | Channel | Normal Condition | Alarm Condition |
|---|---|---|---|
| Longitudinal Beam | 0 | Base reflection response | Lack of Base response |
| Longitudinal Beam | 1 | Absence of Web area response | Unexpected Web area response |
| Top Web | 2N | Side wall response | Lack of side wall response |
| Top Web | 2P | Absence of response | Unexpected upper web response |
| Middle Web | 3N | Side wall response | Lack of side wall response |
| Middle Web | 3P | Absence of response | Unexpected middle web response |
| Bottom Web | 4N | Side wall response | Lack of side wall response |
| Bottom Web | 4P response | Absence of web response | Unexpected lower |
| Angle Beam Left | 5 | Absence of response | Unexpected base area response |
| Angel Beam Right | 6 | Absence of response | Unexpected base area response |

As shown in Table 1, the longitudinal beam transducer provides two alarm conditions, the first being a lack of response from the base area of the rail and the second being an unexpected response found in the web area of the rail. Similarly each of the web transducers provide two responses; the first being a lack of a response from the side wall of the web and the second being an unexpected response within the web itself. The two bottom rail transducers each provide one alarm condition, that being an unexpected response in the base area of the rail.

Figure 4:
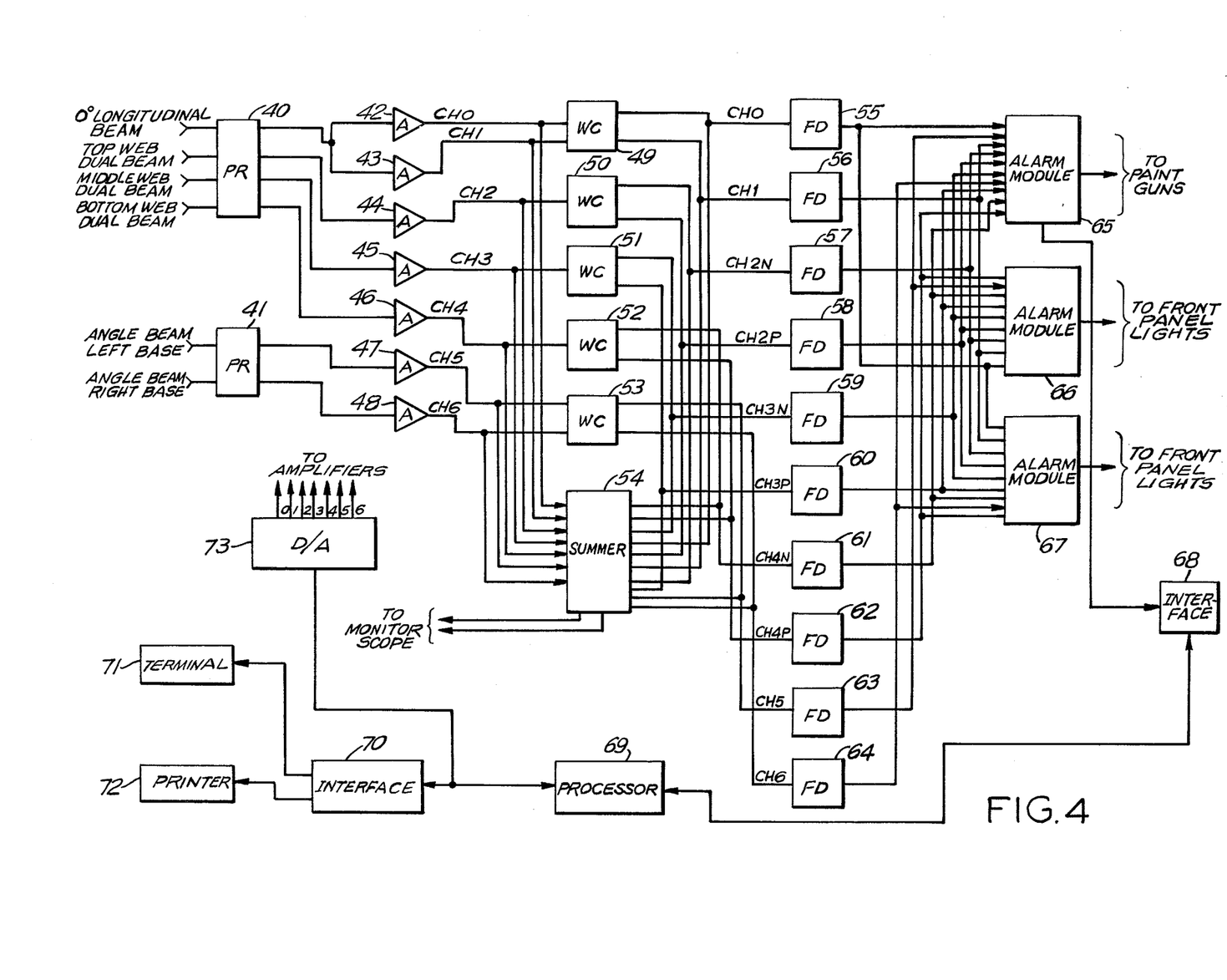
FIG. 4 illustrates a schematic block diagram of the rail inspection equipment of the instant invention.

Referring now to FIG. 4, there is illustrated a schematic block diagram of the apparatus of the instant invention. The entire system is controlled by microprocessor 69 which is interfaced to operator terminal 71 through interface circuitry 70, while information for the operator is printed on printer 72, also connected to micro-processor 69 by interface 70. Micro-processor 69 is preferably a Z80A microcomputer, while printer 72 and terminal 71 can be any appropriate equipment capable of operating with the chosen micro-processor. Interface 70 consists of standard circuitry necessary to interface input/output equipment with a micro-processor.

During normal operation the system shown in FIG. 4 is programmed by the operator (via micro-processor 69 and terminal 71) to view each rail under test as a series of rail pieces called segments. For each rail segment the system sensitivity to flaw detection can be set to one of two pre-programmed values, designated high sensitivity or low sensitivity. By altering system sensitivity in this manner different rail segments can be tested at varying sensitivities as required by the testing standards of the manufacturer and/or the user.

In addition to the micro-processor and I/O circuitry described above, the system consists of five basic sections. The first section consists of pulser/receiver transducers 40 and 41, which transmit the ultrasonic pulses into the rail and receive the responses from the rail. The second section consists of amplifiers 42 through 48 which are preprogrammed by the processor in a manner to be described below to provide varying gains for the responses from the transducers. The third section consists of "window circuits" 49 through 53. These circuits, as will be described in more detail below, provide both positive and negative window gates to select certain response signals from the transducers. The fourth section consists of flaw detectors 55 through 64. Each flaw detector is designed to detect the occurrence of a flaw on a particular transducer channel. That is, flaw detector 55 is responsive to flaws detected on channel zero, which is the longitudinal beam lack of base response, while flaw detector 56 detects flaws on channel 1, which is the longitudinal beam unexpected web response. The manner in which each flaw detector operates, will also be described below. The fifth major section of the apparatus consists of alarm modules 65 through 67. The alarm modules receive flaw detection signals from the flaw detectors and translate those signals into an appropriate operator indication such as lighting predetermined front panel lights and/or operating a paint gun on the apparatus to mark the position on the rail where the flaw is detected. Still other sections of the apparatus consist of interface circuit 68 which interfaces micro-processor commands with the alarm module for the paint guns, summer circuit 54, which sums signals from the amplifiers and the window circuits for display on a monitor scope and Digital to Analog (D/A) converter 73, which functions to translate binary words from micro-processor 69 into analog voltages which control the gain of amplifiers 42 through 48 in the manner described below.

Referring now to FIG. 4 in greater detail, pulser receiver transducers 40 and 41 can be of the type described in U.S. Pat. No. 4,004,455 or other equivalent ultrasonic transducers of the type well known in the art. Transducer 40 operates to provide ultrasonic pulses for alarm channels zero through 4N, while transducer 41 provides transducer pulses for alarm channels 5 and 6. Both transducers 40 and 41 are essentially identical and provide the same function of generating the high voltage "main bang" pulse shown in FIG. 3 and amplifying the response signal by approximately 20 db. The amplification of the response signal provided by each of transducers 40 and 41 is fixed and not variable. It is to be understood that each of the transducers are controlled by a free running pulse generator, such as is described in U.S. Pat. No. 4,004,455 and are not driven by a speed related pulse generator.

The signals received by transducers 40 and 41 are applied to amplifiers 42 through 48, wherein each of the amplifiers provides amplification for a separate alarm channel as indicated in FIG. 4. The net gain of each of amplifiers 42 through 48 is variable from approximately zero db to 66 db over and above the 20 db fixed amplification level provided by transducers 40 and 41. Each amplifier gain is individually programmable and can be changed automatically over the length of a rail under test to alter the gain of the system for various rail sections. This is accomplished by proper instructions to micro-processor 69 which provides a unique binary word for each amplifier to D/A converter 73. The D/A converter, in turn, generates a gain signal to be applied to individual ones of amplifiers 42 through 48. In one preferred embodiment of the invention the gain for each amplifier can be set to a high or a low value although of course it should be understood that the amplifier gain could be varied in any number of discreet steps over its entire range of amplification. It should also be understood that micro-processor 69 sets the gain in amplifiers 42 through 48 as a gain differential over the fixed gain supplied by pulser receivers 40 and 41. Therefore, if a particular amplifier is programmed with a zero db gain differential, the net gain for the system will be 20 db. The details of amplifiers 42 through 48 will be described in greater detail below.

Window circuits 49 through 53 are utilized to select response areas for triggering the associated flaw detectors. The windows or gates are created by counting circuits included within the window circuits synchronized to the wheel/rail interface pulse described above in connection with FIG. 3. Both the time position of a gate relative to the wheel/rail interface (delay) and gate width are user adjustable by front panel controls on the apparatus (not shown). In a preferred embodiment of the invention, each increment of gate delay and width is adjustable in 1.25 microsecond intervals.

Figure 5:
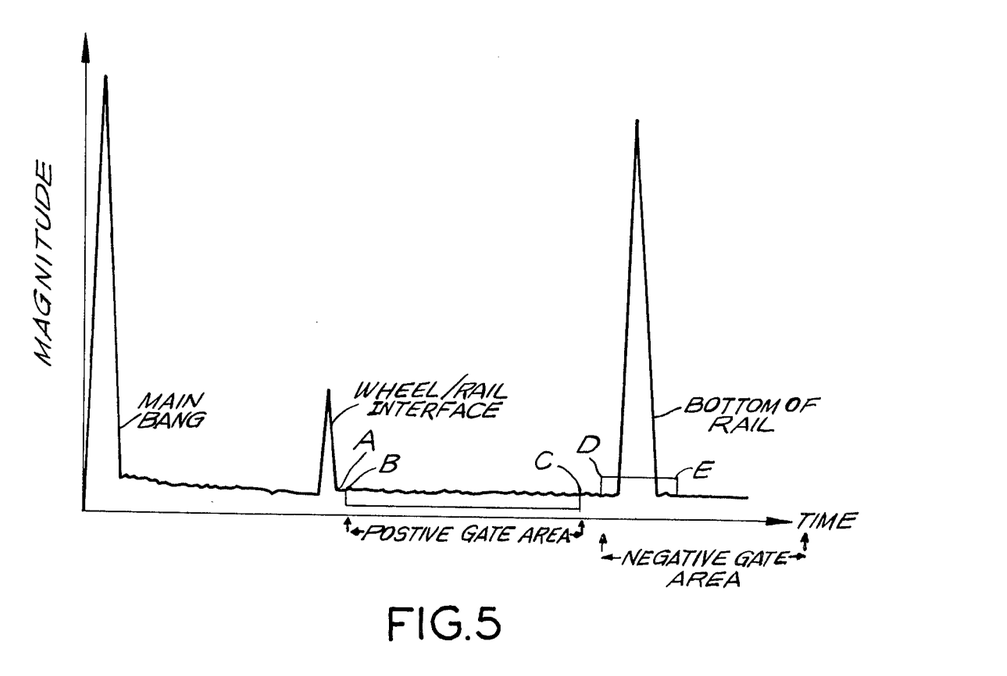
FIG. 5 is a second time vs. magnitude response illustrating the positive and negative gating scheme used with the instant invention.

More particularly, referring to FIG. 5, there is illustrated the main bang transducer pulse and the wheel/rail interface discussed above. Point A designates the conclusion of the wheel/rail interface pulse. The distance between points A and B represents the variable delay between the conclusion of the wheel/interface pulse and the commencement of the positive gate area. The distance between points B and C represents the user adjustable width of the positive gate area, the distance between points C and D represents the adjustable delay between the conclusion of the positive gate area and the commencement of the negative gate area and the distance between points D and E represents the width of the negative gate area.

Typically, the positive gate area is used to window response signals in the unexpected response areas, i.e. in those areas in which flaws may occur. In FIG. 5, the positive gate area is centered in the area between the wheel rail interface and the bottom of the rail, which for the longitudinal transducer is the area in which flaws could occur. The negative gates are utilized to window response areas in the expected response areas and in FIG. 5 the negative gate area windows the transducer pulse occurring at the bottom of the rail.

Referring again to FIG. 4, it can be appreciated that each of window circuits 49 through 53 can, by adjustment of the position and width of the positive and negative gate areas, select particular response signals expected on each of the alarm channels. For example, the positive and negative gates for channels zero and one, i.e. the longitudinal beam base response and the longitudinal beam web response would be set as shown in FIG. 5. With this configuration, logic within window circuit 49 would check for the occurrence of the base response signal during the interval set by the negative gate area.

If a response was detected within the negative gate area, this would indicate a normal condition and alternatively, if there was a lack of a base response within the negative gate area, this would indicate an alarm condition. Similarly, for the web area, if a response was detected within the positive gate area, this would indicate an unexpected or alarm condition, while alternatively if no response was detected within the positive gate area, this would indicate a normal condition. The position of the particular gate for each alarm channel is set by front panel controls and the respective positions after setting can be monitored on a monitor scope attached to summer circuit 54 with the monitor scope providing an indication such as is shown in FIG. 5. In this way the operator can adjust the positive and negative gates for each alarm channel and appropriate logic within window circuits 49 through 53 will generate an alarm condition when an unexpected response occurs, or when there is a lack of an expected response. A more detailed description of the window circuits will be described below. Summer circuit 54 simply sums the appropriate input signals for display, a function well known in this technical area, and thus summer circuit 54 will not be described in further detail.

Each of flaw detectors 55 through 64 operate for a particular alarm channel and each of the flaw detectors contains a counter driven by pulses from a shaft encoder (not shown). As described above, the shaft encoder generates pulses every 1/16th of an inch of the rail under test.

Flaw detectors 55 through 64 operate in essentially the same manner as did counters 14, comparator 16 and variable count switches 32 in FIG. 1. That is, in the absence of an alarm condition, the counters within the flaw detectors are held in a reset state. When an alarm condition occurs, the counter is allowed to count up. By presetting an alarm count threshold, the flaw detector will count up to the preset threshold and continually alarm thereafter until either the alarm condition passes or the flaw detector reset switch (not shown) is depressed. Once cleared, the flaw detector will begin counting again as soon as an alarm condition occurs. Setting a particular threshold count into the counters contained within the flaw detectors, or resetting the counters, is controlled by front panel controls (not shown). It is, of course, understood that each of flaw detectors 55 through 64 contain a counter such as counter 14, a comparator such as comparator 16, and variable count switches such as switches 32 in FIG. 1.

The outputs from the flaw detectors are applied to alarm module 65, alarm module 66, and alarm module 67. Alarm module 65 operates paint guns in response to alarm signals being received from any or all of the various flaw detectors. The paint guns (not shown) operated in response to outputs from alarm module 65, mark detected rail flaws and are generally driven by unexpected responses. Alarm modules 66 and 67 are utilized to control front panel indicator lights used to signal both the occurrence of unexpected responses, as well as the loss of expected responses. It is necessary to indicate the lack of expected responses as this may be a sign of inadequate coupling between the test apparatus and the rail under test, a condition which may lead to inaccurate test results. Alarm module 65, which controls the paint guns, may also operate pursuant to a delay algorithm contained within system micro-processor 69 to allow synchronization of the appearance of the flaw with the position of the paint guns. Interface 68 allows micro-processor 69 to communicate with the alarm module for synchronization of the paint gun operation.

Micro-processor 69 is preferably a Zilog Z80A micro-processor, along with related circuitry, sufficient to operate with terminal 71 and printer 72 via interface 70. Micro-processor 69 automatically begins execution of its program when power is applied to the circuitry, or alternatively could be operated with activation of a reset switch (not shown) on interface 70. When a rail under test enters the apparatus, a shaft encoder "rides" on the rail and sends distance pulses to the micro-processor which in turn uses this information to measure rail segments. The micro-processor is programmable via terminal 71 through which the system operator enters system commands while receiving output data via printer 72. The primary function of micro-processor 69 is to measure rail segments as the rail is tested and to adjust system gain via amplifiers 42 through 48 for each particular segment under test. Micro-processor 69 operates amplifiers 42 through 48 via d/a converter 73, which converts an eight bit binary code word sent by processor 69, into an analog voltage required to vary the gain of amplifiers 42 through 48 in a manner to be described below.

Figure 6A:
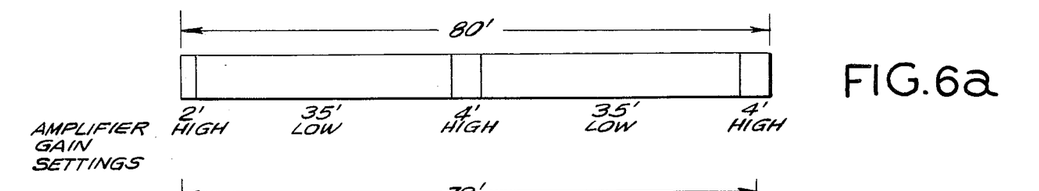
FIGS. 6A and 6B illustrate the manner in which rails may be segmented with the inventive rail testing apparatus.
Figure 6B:
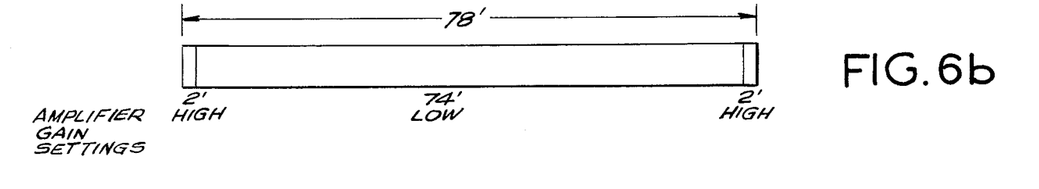

The system operator may program micro-processor 69 to vary the amplifier gains according to the section of rail currently under test. Each amplifier may preferably have two different gain settings defined by the operator, a high gain and a low gain, and in one embodiment of the invention the operator can then specify up to five rail segments of varying lengths. FIG. 6A illustrates a rail having five segments along with the indicated high and low amplifier gain settings, while FIG. 6B illustrates a second rail having three segments with respective high and low gain settings. It is to be understood, of course, that through proper programming of micro-processor 69, the rail could be divided into any number of segments with gain settings varying per segment.

Figure 7:
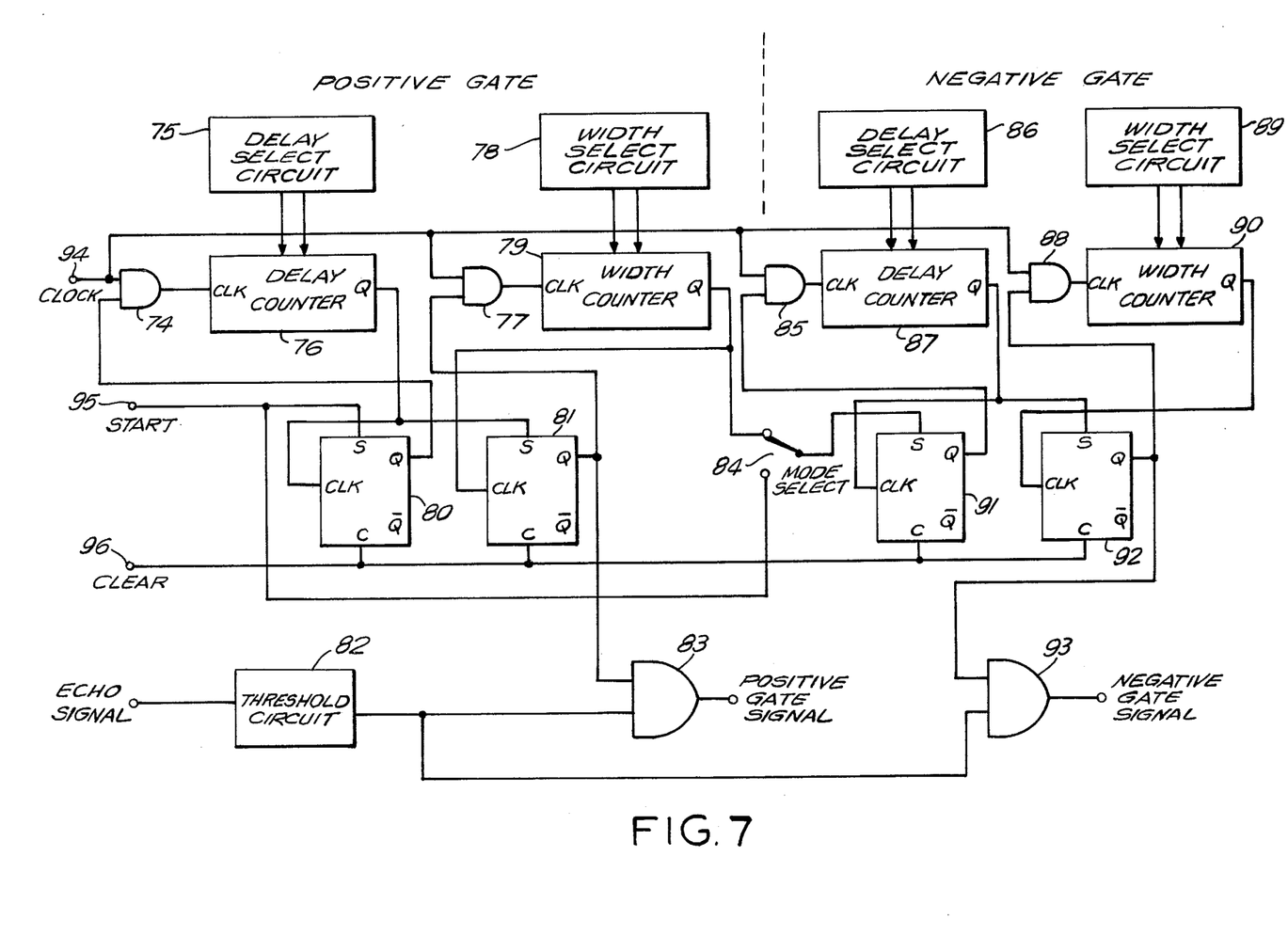
FIG. 7 is a schematic block diagram of the positive and negative gating circuitry.

Referring now to FIG. 7, there is shown a particular embodiment for the window circuits described above with respect to FIG. 4. The circuit shown in FIG. 7 provides both a positive and negative gate indication as previously described and it is to be understood that each window circuit, such as window circuit 49, contains one circuit of the type shown in FIG. 7. Also, FIG. 7 is a simplified illustration of one embodiment of a window circuit and it would be apparent to one skilled in this technical area that various circuits could be added to the circuitry shown in FIG. 7 to provide timing and control functions necessary to operate in particular applications of the instant invention.

Applied to terminal 94 is an internal clock pulse with a period of approximately 1.25 microseconds. The clock is applied to one input of AND gates 74, 77, 85 and 88 and via these gates, in a manner to be described below, is also applied to counters 76, 79, 87 and 90. Counters 76 and 79, along with select circuits 75 and 78 and flip-flops 80 and 81 generally describe the positive gate circuitry. Similarly, counters 87 and 90 along with select circuits 86 and 89, and flip-flops 91 and 92 generally describe the negative gate circuitry.

Each of counters 76, 79, 87 and 90 are count-down counters with counter 76 determining the width of the delay period, shown as interval A through B in FIG. 5, with counter 79 determining the interval B through C in FIG. 5, counter 87 determining the width of the interval C through D in FIG. 5, and counter 90 determining the interval D through E in FIG. 5. Connected to delay counter 76 is a delay select circuit 75. The purpose of the delay select circuit is to preset a predetermined count in delay counter 76. In a preferred embodiment of the invention the delay select circuit will preset a particular count into delay counter 76 upon activation of the test apparatus and in addition the delay select circuit can include the ability to allow the preset count to be varied during operation if desired. Width select circuit 78, delay select circuit 86 and width select circuit 89 perform the same functions for width counter 79, delay counter 87 and width counter 90 respectively. Although specific details of circuits 75, 78, 86 and 89 are not shown it is understood that circuitry necessary to preset counts into a count-down counter such as is shown in FIG. 7 would be apparent to one skilled in this technical area.

Start terminal 95 receives a start pulse to begin the sequence of initiating the positive and negative gate sequences. The start pulse could be generated at any time during the test sequence, but preferably is generated by the occurrence of the wheel rail interface pulse shown in FIG. 5 to initiate the occurrence of both the positive and negative gate areas with their respective delays.

Assume that a particular count has been preset into each of counters 76, 79 87 and 90. Upon receipt of a start pulse at terminal 95, flip-flop 80 is placed in the SET state, causing a logical "1" voltage level to be applied to one input of AND gate 74, enabling gate 74 and applying the clock to the clock input of counter 76. This commences interval A-B in FIG. 5 from its preset count and at the conclusion of the count down sequence, a logical "1" level appears at the Q terminal. This logical "1" level toggles flip-flop 80 causing its logical "1" output to go to a logical "0" thereby disabling gate 74 and concluding the positive gate delay period (A-B in FIG. 5).

Simultaneously, the output of counter 76 sets flip-flop 81, applying a logical "1" level to AND gate 77. Application of the logical "1" level to AND gate 77 applies the clock signal to the clock input of width counter 79, commencing its countdown sequence from its preset count and starting the width interval of the positive gate (B-C in FIG. 5). At the same time, the application of a logical "1" from the Q output of flip-flop 81 is applied to positive gate 83, enabling this gate. If a return signal is received on a return echo from the ultrasonic transducers, while this gate is enabled, and if this signal surpasses the threshold level preset in threshold circuit 82, a positive gate signal is generated and applied to the flaw detectors shown in FIG. 4 to indicate the occurrence of a return signal during the positive gate period. Threshold circuit 82 is preset to a particular level to avoid spurious responses resulting from noise signals.

At the conclusion of the countdown sequence of counter 79, its Q output generates a logical "1" signal, toggling flip-flop 81, clearing this flip-flop and applying a logical "0" to both AND gate 77 and AND gate 83. This disables both gates, completing the countdown sequence of counter 79 and concluding the width interval of the positive gate signal.

Mode select switch 84 enables the negative gate interval to commence upon the conclusion of the positive gate interval. More particularly, assuming mode select switch 84 is in the position shown in FIG. 7 the logical "1" level appearing at the output of counter 79, upon the conclusion of its count sequence, will set flip-flop 91, applying a logical "1" level to AND gate 85, thereby applying the clock signal to the clock input of counter 87. This operation commences the countdown of counter 87, and the delay interval of the negative gate (C-D in FIG. 5). Upon the conclusion of the countdown of counter 87, the logical "1" level appearing at its Q output clears flip-flop 91 and sets flip-flop 92, enabling the countdown sequence of counter 90, enabling negative gate 93 and commencing the width interval of the negative gate (D-E in FIG. 5). If a return signal appears during this interval, it will be transmitted to the flaw detectors indicating a flaw during the negative gate interval.

Alternatively mode select switch 84 can be operated in a second mode in which a start pulse from terminal 95 can be applied to the mode select switch and used to set flip-flop 91. In this way, both the positive and negative gates can be made to operate independently. Terminal 96 functions to clear flip-flops 80, 81 and 91 and 92 in accordance with the operation of the circuitry in FIG. 4 with it being understood that additional circuitry of standard design not shown in FIG. 7, could be utilized to permit operation of the window circuit for various applications of the instant invention.

Figure 8:
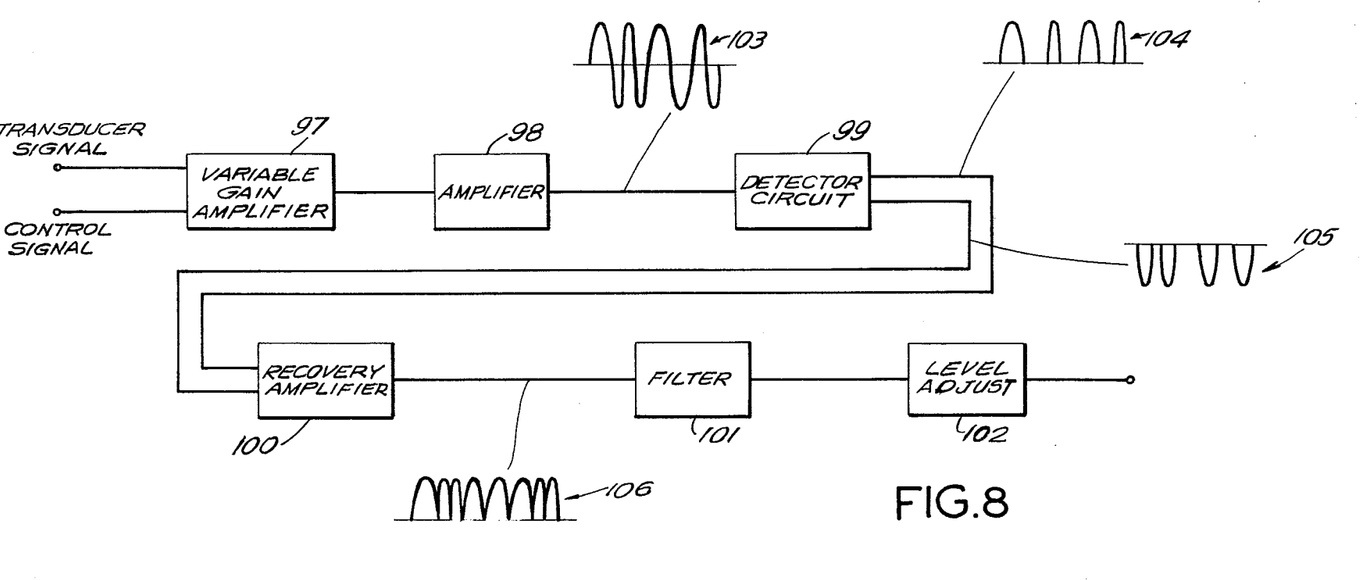
FIG. 8 is a schematic block diagram of the variable amplification circuitry of the instant invention.

Referring now to FIG. 8, there is shown a more detailed block diagram of variable gain amplifiers 42 through 48 previously described in FIG. 4. More particularly, amplifier 97 is a variable gain amplifier which could consist in part, for example, of wide band amplifier with AGC manufactured by Motorola Semi-Conductor Products Inc. with the designation MC1590. The function of variable gain amplifier 97 is to vary the gain of the transducer signal applied thereto in response to the level of the control signal as described above with respect to FIG. 4. The control signal is applied to the amplifier from d/a converter 73, while the transducer signal is received from pulser-receiver 40 or 41. It is to be understood that each of amplifiers 42 through 48 contain the circuitry shown in FIG. 8.

At the output of variable gain amplifier 97 is an additional amplifier 98 producing wave form 103 representing an amplified transducer return signal. Detector circuit 99 operates as a dual halfwave rectifier to generate both the positive half of waveform 103, (wave form 104) and the negative half of waveform 103 (waveform 105). Waveforms 104 and 105 are applied to recovery amplifier 100 which inverts waveform 105 and combines waveforms 104 and 105 to produce the waveform shown at 106. This waveform is filtered by filter 101, applied to a level adjust circuit 102 and from there applied to the window circuits in the manner described above. The level adjust circuitry can be included in the front panel controls (not shown) of the test apparatus.

The instant invention is directed to an ultrasonic nondestructive testing system intended for use in the rail mill environment for complete preshipment testing of rails. Through use of this invention a rail manufacturer can guarantee the integrity of its product to customers while also maintaining tighter controls on its own rail manufacturing process. And because the apparatus of the instant invention is programmable, the rail manufacturer can customize the rail testing procedure according to each customer's requirements for the quality of the rail it purchases.

Advantageously, the instant invention allows the system operator to define critical rail testing parameters. By varying these parameters, varying degrees of system sensitivity can be programmed for different areas of a rail under test. This, for example, allows railend areas to be more closely tested than non-railend areas. This feature allows selective degrees of quality control over the rail product.

Although a specific embodiment of this invention has been shown and described it will be understood that various modifications may be made without departing from the spirit of this invention.

We claim:

1. Apparatus for detecting flaws in a railroad rail, the apparatus comprising;
    means for transmitting ultrasonic signals into the railroad rail and for receiving associated echo signals from within the railroad rail;
    distance measuring means for measuring the length of the railroad rail;
    micro-processor means for dividing the railroad rail into a plurality of rail segments, said micro-processor means being responsive to operator-supplied data and to said distance measuring means for determining a length of each of said rail segments;
    means for selectably applying predetermined amounts amplification to said associated echo signals received from within each of said plurality of rail segments; and
    means responsive to said selectably amplified echo signals for providing indications of flaws within the railroad rail.

2. Apparatus in accordance with claim 1 wherein there is further included means for selectively applying said amplified echo signals from said supplying means to said providing means.

3. Apparatus in accordance with claim 2 wherein said selectively applying means includes positive gating means and negative gating means, said positive gating means for applying unexpected echo signals to said providing means and said negative gating means for applying expected echo signals to said providing means.

4. Apparatus in accordance with claim 3 wherein said providing means includes means responsive to the presence of unexpected echo signals for generating a signal indicative of a flaw within the railroad rail and means responsive to the absence of an expected echo signal for generating a signal indicative of signal loss from the railroad rail.

5. Apparatus in accordance with claim 1 wherein said micro-processor means further includes means responsive to operator supplied input data for setting the amount of amplification provided to said associated echo signals for each of said plurality of measured rail segments.

6. Apparatus for detecting flaws in a railroad rail, the apparatus comprising;
    means for transmitting ultrasonic signals into the railroad rail and for receiving associated echo signals reflected from within the railroad rail;
    distance measuring means for measuring the length of the railroad rail;
    micro-processor means responsive to operator provided input data and to said distance measuring means for dividing the railroad rail into a plurality of predetermined measured rail segments and for applying predeterminable amounts of amplification to said associated echo signals received from said predetermined measured rail segments of the railroad rail;
    means responsive to said amplified echo signals for providing indications for flaws within the railroad rail; and
    means for selectively transferring said amplified echo signals from said supplying means to said providing means.

7. Apparatus in accordance with claim 6 wherein said selectively transferring means includes positive gating means and negative gating means, said positive gating means for applying unexpected echo signals to said providing means and said negative gating means for applying expected echo signals to said providing means, 8. Apparatus in accordance with claim 7 wherein said providing means includes means responsive to the presence of unexpected echo signals for generating a signal indicative of a flaw within the railroad rail and means responsive to the absence of expected echo signals for generating a signal indicative of signal loss from the railroad rail.

* * * * *